(12) United States Patent
Vindler et al.

(10) Patent No.: US 9,017,147 B2
(45) Date of Patent: Apr. 28, 2015

(54) SURFACE SAMPLE COLLECTION TOOL

(75) Inventors: Michael R. Vindler, Pittsburgh, PA (US); Ronald H. Lovett, Verona, PA (US)

(73) Assignee: Siemens Energy, Inc., Orlando, FL (US)

(*) Notice: Subject to any disclaimer, the term of this patent is extended or adjusted under 35 U.S.C. 154(b) by 1044 days.

(21) Appl. No.: 13/089,478

(22) Filed: Apr. 19, 2011

(65) Prior Publication Data
US 2012/0266733 A1 Oct. 25, 2012

(51) Int. Cl.
*B26D 3/10* (2006.01)
*B23D 61/18* (2006.01)
*B23D 45/00* (2006.01)
*B26D 1/44* (2006.01)
*G01N 1/04* (2006.01)
*G01N 1/06* (2006.01)
*G01N 1/08* (2006.01)

(52) U.S. Cl.
CPC .............. *B23D 61/18* (2013.01); *B23D 45/003* (2013.01); *B26D 1/44* (2013.01); *B26D 3/10* (2013.01); *G01N 1/04* (2013.01); *G01N 1/06* (2013.01); *G01N 1/08* (2013.01)

(58) Field of Classification Search
CPC .......... G01N 1/02; B26D 1/44; B23D 45/003; B23D 31/00
USPC ............ 83/886, 887, 861; 451/236, 280, 541; 73/864.41
See application file for complete search history.

(56) References Cited

U.S. PATENT DOCUMENTS

| | | | | | |
|---|---|---|---|---|---|
| 2,015,873 | A | * | 10/1935 | Schlumberger | 175/17 |
| 2,237,570 | A | * | 4/1941 | Maillart | 228/103 |
| 2,237,571 | A | * | 4/1941 | Maillart | 83/745 |
| 2,354,399 | A | * | 7/1944 | Noble | 175/77 |
| 2,389,208 | A | * | 11/1945 | Orr | 175/77 |
| 2,542,474 | A | * | 2/1951 | Burchett | 37/92 |
| 2,599,405 | A | * | 6/1952 | Mennecier | 175/40 |
| 2,688,369 | A | * | 9/1954 | Broyles | 166/100 |
| 3,178,816 | A | * | 4/1965 | Schmid | 30/228 |
| 3,630,296 | A | * | 12/1971 | Bullard | 175/77 |
| 3,709,094 | A | * | 1/1973 | Laux | 409/132 |
| 3,857,425 | A | * | 12/1974 | Wiklund | 144/34.1 |
| 3,877,159 | A | * | 4/1975 | Boomstra | 37/326 |
| 3,968,821 | A | * | 7/1976 | Jonsson | 144/34.1 |
| 4,106,561 | A | * | 8/1978 | Jerome et al. | 166/55.2 |
| 4,304,139 | A | * | 12/1981 | Johnson | 73/864.32 |
| 4,449,593 | A | * | 5/1984 | Jageler et al. | 175/58 |
| 4,455,910 | A | * | 6/1984 | Kraft et al. | 83/874 |

(Continued)

FOREIGN PATENT DOCUMENTS

EP 1413872 A2 * 4/2004
FR 2756631 A1 * 6/1998

(Continued)

*Primary Examiner* — Lee D Wilson
*Assistant Examiner* — Joel Crandall (57) ABSTRACT

A sampling device for removing a surface portion from a substrate. The device includes a frame structure and a cutter head assembly. The cutter head assembly includes a pivot body having a first end supported at a pivot point on the frame structure, and a cutter supported for rotation about a rotational axis at a second end of the pivot body. The cutter has a semi-ellipsoidal shape and a drive motor is operably connected to the cutter. The pivot point is located in spaced relation to the rotational axis. The cutter is operable to cut a surface portion of a substrate during pivotal movement about the pivot point.

17 Claims, 6 Drawing Sheets

(56) References Cited

U.S. PATENT DOCUMENTS

| | | | |
|---|---|---|---|
| 4,746,858 A | 5/1988 | Metala et al. | |
| 4,773,799 A | 9/1988 | Guironnet | |
| 4,845,896 A * | 7/1989 | Mercaldi | 451/121 |
| 4,856,233 A * | 8/1989 | Mercaldi | 451/28 |
| 4,925,621 A * | 5/1990 | Muth et al. | 376/262 |
| 5,569,393 A * | 10/1996 | Reinhart et al. | 219/69.15 |
| 5,867,909 A * | 2/1999 | Jeltsch et al. | 30/228 |
| 5,894,096 A * | 4/1999 | Kotraba et al. | 73/864.63 |
| 5,929,347 A * | 7/1999 | Matsuura et al. | 73/863.01 |
| 5,984,766 A * | 11/1999 | Gilmour | 451/211 |
| 7,012,495 B2 | 3/2006 | Underwood et al. | |
| 7,647,681 B1 * | 1/2010 | Harris et al. | 29/281.1 |

FOREIGN PATENT DOCUMENTS

| | | | |
|---|---|---|---|
| GB | 2282778 A * | 4/1995 | |
| JP | H0633046 B2 | 5/1994 | |
| JP | H07104229 B2 | 11/1995 | |
| JP | H2001317284 A | 11/2001 | |
| WO | WO9117001 A1 * | 11/1991 | |

* cited by examiner

SURFACE SAMPLE COLLECTION TOOL

FIELD OF THE INVENTION

The present invention relates to devices for taking material samples and, more particularly, to devices for removing a portion of the surface of a base material for use as a test sample.

BACKGROUND OF THE INVENTION

It is often necessary to analyze the physical characteristics of a structure by removal of a portion of the structure for testing. In particular, systems that include hostile environments, such as may be provided in power plants, are often exposed to mechanical and thermal stress that can result in deterioration of components including, for example, power plant turbine components and piping.

There is a need for a means for determining the condition of the material in components to facilitate an evaluation of whether a maintenance operation is required, and to predict a useful life for the components. Further, there is a need to provide a means for obtaining material samples from components while reducing adverse effects that may result from the material removal.

SUMMARY OF THE INVENTION

In accordance with an aspect of the invention, a sampling device is provided for removing a surface portion from a substrate. The device comprises a frame structure and a cutter head assembly. The cutter head assembly comprises a pivot body having a first end supported at a pivot point on the frame structure, and a cutter supported for rotation about a rotational axis at a second end of the pivot body. The cutter comprises a shape defined by a rotation of a conic having a circular cutting end. A drive motor is operably connected to the cutter, and the pivot point is located in spaced relation to the rotational axis. The cutter is operable to cut a surface portion of a substrate during pivotal movement about the pivot point.

The shape of the cutter may comprise a semi-ellipsoidal shape adapted to remove an elliptically shaped surface portion from the substrate.

The pivot point may be located a distance from the rotational axis that is greater than a radius of the circular cutting end.

The drive motor may be movable relative to the frame structure in a longitudinal direction, and a linkage may be provided between the drive motor and the pivot body, the linkage transmitting longitudinal movement of the drive motor into pivotal movement of the pivot body.

A drive shaft may extend adjacent to the linkage for transmitting rotational movement from the drive motor to the cutter.

A stepper motor may be operably coupled to the drive motor to move the drive motor in the longitudinal direction.

Adjusting members may be provided movable relative to the frame structure to define an adjustable predetermined depth for the cutter to penetrate the substrate.

Clamp members may be provided comprising magnets mounted to the frame structure for engagement with the substrate.

The frame structure may include a housing assembly having side portions, and the clamp members may be slidably positionable along the side portions. Locking members may be provided that are adapted to lock the clamp members to predetermined positions along the side portions.

In accordance with another aspect of the invention, a sampling device is provided for removing a surface portion from a substrate. The device comprises a frame structure including a base side. A cutter mechanism is provided including a cutter movable in a vertical direction to extend from the base side into engagement with the substrate. A plurality of height adjusting members extend from the base side to engage the substrate. The height adjusting members are movable relative to the frame structure and relative to the cutter to define an adjustable predetermined depth for the cutter to penetrate the substrate. A plurality of clamp members comprising magnets are mounted to the frame structure for engagement with the substrate to retain the frame structure at predetermined height positions relative to the substrate, as defined by the height adjusting members.

The frame structure may include a housing assembly having side portions, and the clamp members may be mounted to the side portions, the clamp members being adjustable in the vertical direction along the side portions to positions corresponding to the predetermined height positions.

A locking member may be associated with each of the clamp members, and the locking members may be adapted to lock the clamp members to the side portions at the predetermined height positions.

The clamp members may be supported for pivotal movement relative to the frame structure, and the magnets may comprise switchable magnets.

The cutter mechanism may be included in a cutter head assembly comprising a pivot body having a first end supported at a pivot point on the frame structure, and a cutter supported for rotation about a rotational axis at a second end of the pivot body. The cutter may comprise a shape defined by a rotation of a conic having a circular cutting end, and a drive motor may be provided operably connected to the cutter for driving the cutter in rotational movement.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

DETAILED DESCRIPTION OF THE INVENTION

In the following detailed description of the preferred embodiment, reference is made to the accompanying drawings that form a part hereof, and in which is shown by way of illustration, and not by way of limitation, a specific preferred embodiment in which the invention may be practiced. It is to be understood that other embodiments may be utilized and that changes may be made without departing from the spirit and scope of the present invention.

Figure 1:
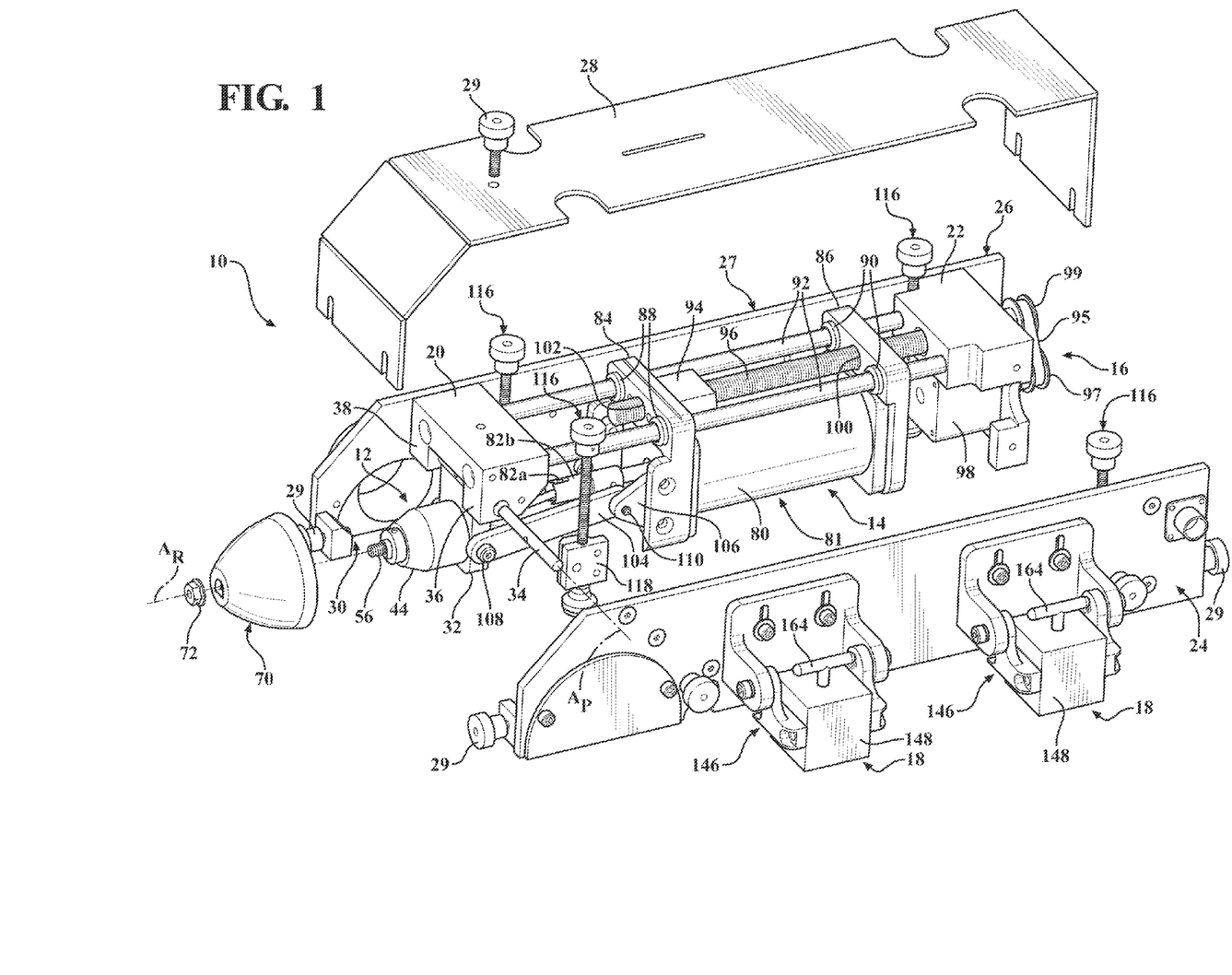
FIG. 1 illustrates a partially exploded view of a sampling device in accordance with an aspect of the present invention.

Referring to FIG. 1, a sampling device 10 for removing a surface portion from a substrate in accordance with an aspect of the present invention is shown. The sampling device 10 generally includes a cutter head assembly 12, a main drive assembly 14, a case assembly or frame structure 16 and a plurality of clamping assemblies or clamp members 18.

The frame structure 16 includes a front lateral member 20 and a rear lateral member 22 spaced longitudinally from the front lateral member 20. The front and rear lateral members 20, 22 may comprise blocks, such as metal blocks, forming rigid cross members configured to provide supports for components of the sampling device 10, as is described further below. First and second side portions 24, 26, comprising plate structures, define longitudinally extending members that are rigidly fastened to sides of the front and rear lateral members 20, 22 to form the frame structure 16 as a substantially rigid box-like structure. In addition, an upper cover 28 may be provided attached to the lateral member 20 and to the side portions 24, 26 by attachment screws 29 to close an open upper side 27 of the frame structure 16, while a lower or base side 30 of the frame structure 16, remains generally open. The side portions 24, 26 and upper cover 28 form a housing assembly for the sampling device 10.

It should be noted that reference to relative directions such as lateral, upper, lower or bottom, and vertical, and similar terms, are used with reference to the orientation of the sampling device 10 as shown in the drawings. However, as will be apparent from the description provided herein, the sampling device may be utilized in various orientations, and the scope of the invention is not intended to be limited by the particular directional conventions selected for description of the sampling device 10.

Figure 2:
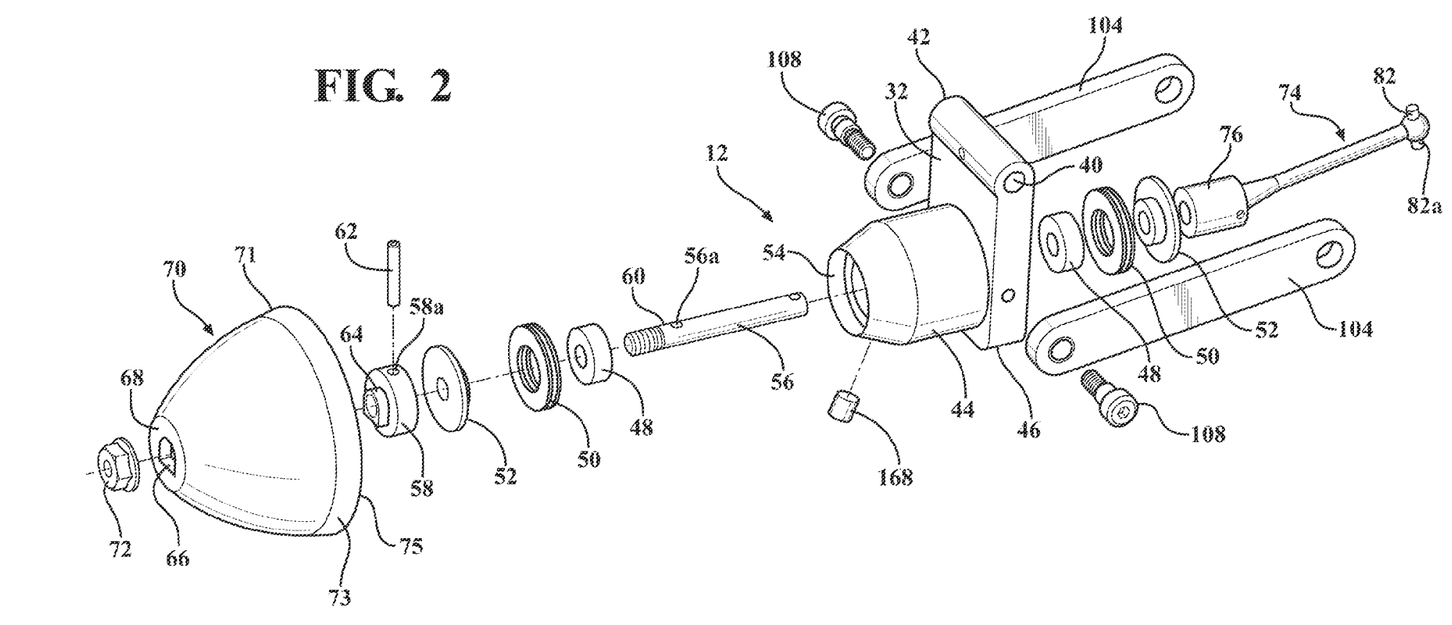
FIG. 2 is an enlarged exploded view of a cutter head assembly for the sampling device.

Referring to FIG. 2, the cutter head assembly 12 includes a pivot body 32 supported on the front lateral member 20. The pivot body 32 is mounted for pivotal movement on a pivot rod 34 extending through an aperture 40 at a first end 42 of the pivot body 32, and extending between a pair of vertical arms 36, 38 of the front lateral member 20, as seen in FIG. 1. The pivot body 32 includes a cutter shaft housing 44 extending from a second end 46 of the pivot body 32. Shaft bearings 48, thrust bearing assemblies 50, and spacers 52 are located in openings 54 (only one shown) at opposing sides of the cutter shaft housing 44. A drive shaft 56 extends through the cutter shaft housing 44 and is supported on the pivot body 32 by the shaft bearings 48. The drive shaft 56 is supported for rotation about a rotational axis $A_R$ extending the length the drive shaft 56 and oriented substantially perpendicular to a generally vertical plane defined by the pivot body 32.

A cutter mount 58 is located on a front end 60 of the drive shaft 56. The cutter mount 58 is coupled for rotation with the drive shaft 56 by a pin 62 extending through a hole 58a in the cutter mount 58 and through a hole 56a extending through the front end 60 of the drive shaft 56. The cutter mount 58 includes a D-shaped mount portion 64 for engagement in a D-shaped hole 66 formed in a central hub 68 of a cutter 70, such that the cutter 70 is constrained to rotate with the cutter mount 58. A lock nut 72 threadably engages the front end 60 of the drive shaft 56 to retain the cutter 70 on the cutter mount 58. The cutter 70 is generally "bowl" shaped, i.e., a rotation of a conic having a circular cutting end 71, and is described in greater detail below.

The cutter 70 may be formed of a medium carbon content steel. The cutting end 71 is defined by an abrasive cutting surface 73 extending around inner and outer surfaces adjacent an edge 75 of the cutter 70. For example, the cutting end 71 may be defined by a cubic boron nitride material coating extending along the inner and outer surfaces of the cutter 70 approximately ⅜ inch from the edge 75. The abrasive cutting end 71 comprises a slightly greater diameter of the outer surface of the cutter 70, and a slightly smaller diameter of the cutter 70, than the remainder of the cutter 70 due to a thickness of the abrasive coating material. Further, the abrasive cutting surface 73 operates to cut material for removal of the sample 114 with very little applied force to perform the cut without causing a plastic deformation of the material, to thereby substantially avoid alteration of the physical characteristics of the sample 114 due to stress applied by the cutter 70.

Figure 3:
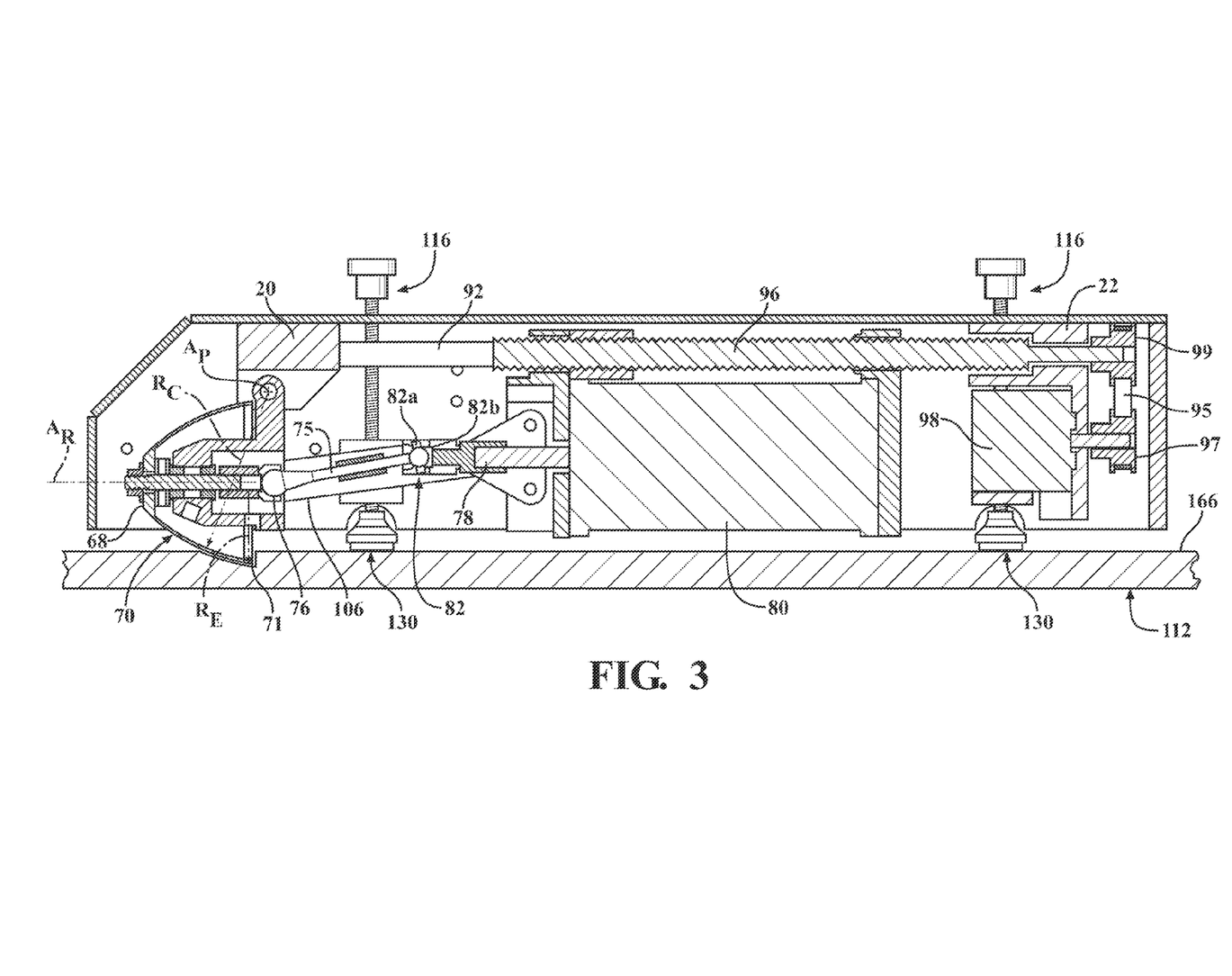
FIG. 3 is a cross-sectional view of the sampling device showing a cutter of the cutter head assembly in a position depicting a partial cut through a substrate.

Referring to FIG. 3, the drive shaft 56 is connected to a transfer shaft assembly 74 comprising a transfer shaft 75. In particular, the drive shaft 56 is connected to the transfer shaft 75 at a first joint 76, and the transfer shaft 75 is connected to an output shaft 78 of an electric motor 80 at a second joint 82. The first and second joints 76, 82 may comprise constant velocity joints. For example, the transfer shaft assembly 74 may comprise a Traxxas drive shaft model number 4951R, available from Traxxas of Plano, Tex. Further, the second joint 82 may comprise a dog bone joint that transfers rotational movement while permitting longitudinal movement of a front portion 82a of the second joint 82 relative to a rear portion 82b of the second joint 82. The transfer shaft assembly 74 and drive shaft 56 transfer a rotational driving movement to the cutter 70, as is described further below.

Referring to FIG. 1, the motor 80 is rigidly mounted to a front motor plate 84 at a front end thereof, and is rigidly mounted to a rear motor plate 86 at a rear end thereof to define a motor assembly 81. The front motor plate 84 includes a pair of front bearings 88, and the rear motor plate 86 includes a pair of rear bearings 90. The frame structure 16 further includes a pair of elongated rails 92. The rails 92 extend between, and are supported by, the front and rear lateral members 20, 22, and each of the rails 92 extends through a respective pair of front and rear bearings 88, 90. Hence, the motor 80 is supported at the bearings 88, 90 for sliding movement in a longitudinal direction along the rails 92.

The front motor plate 84 further includes a threaded block 94 located between the front bearings 88. A threaded or screw shaft 96 extends from a location above a stepper motor 98, through an aperture 100 in the rear motor plate 86 and in threaded engagement in a threaded aperture 102 defined by the threaded block 94. The stepper motor 98 is mounted to the rear lateral member 22 and may be controlled to rotate the screw shaft 96 predetermined amounts. A drive belt 95 connects a drive pulley 97 of the stepper motor 98 to a driven pulley 99 mounted to an end of the screw shaft 96 to transfer rotational driving movement from the stepper motor 98 to the screw shaft 96. Rotation of the screw shaft 96 effects a longitudinal movement of the threaded block 94 relative to the frame structure 16. In particular, rotation of the screw shaft 96 may cause the motor assembly 81 to be driven forwardly or rearwardly relative to the frame structure 16 along the rails 92.

Referring to FIGS. 1 and 2, a linkage defined by a pair of pivot links 104 extends between the motor assembly 81 and the cutter head assembly 12. A first end of each of the pivot links 104 is pivotally attached to the pivot body 32, adjacent to the second end 46 of the pivot body 32, at a first pivot point, and a second end of each of the pivot links 104 is pivotally attached to a link bracket 106, mounted to the front motor plate 84, at a second pivot point. The first and second pivot points may be defined by respective shoulder bolts 108, 110. Hence, the pivot links 104 may transfer longitudinal movement of the motor assembly 81, as effected by actuation of the stepper motor 98, into pivotal movement of the pivot body 32 about a pivot point or pivot axis $A_P$ defined by the pivot rod 34.

Referring additionally to FIG. 3, the first and second joints 76, 82 of the transfer shaft assembly 74 are located generally longitudinally and vertically aligned with the first and second pivot points 108, 110, respectively. The transfer shaft 75 of the transfer shaft assembly 74 extends substantially parallel to the pivot links 104. Hence, the pivot links 104 are provided to transfer a force for pivoting the pivot body 32, while the transfer shaft 75 is provided for transferring a rotational movement to the drive shaft 56 and cutter 70 during pivotal movement of the pivot body 32.

Referring to FIG. 3, it may be seen that the pivot axis $A_P$ for the pivot body 32 is located in spaced relation to the rotational axis $A_R$ of the drive shaft 56, and the surface of the cutter 70 defines a generally constant radius of curvature $R_C$ extending from the cutting end 71 to a location adjacent to the hub 68, centered at the pivot axis $A_P$. In particular, the pivot axis $A_P$ is located a distance from the rotational axis $A_R$ that is greater than a radius $R_E$ of the circular cutting end 71.

Figure 4:
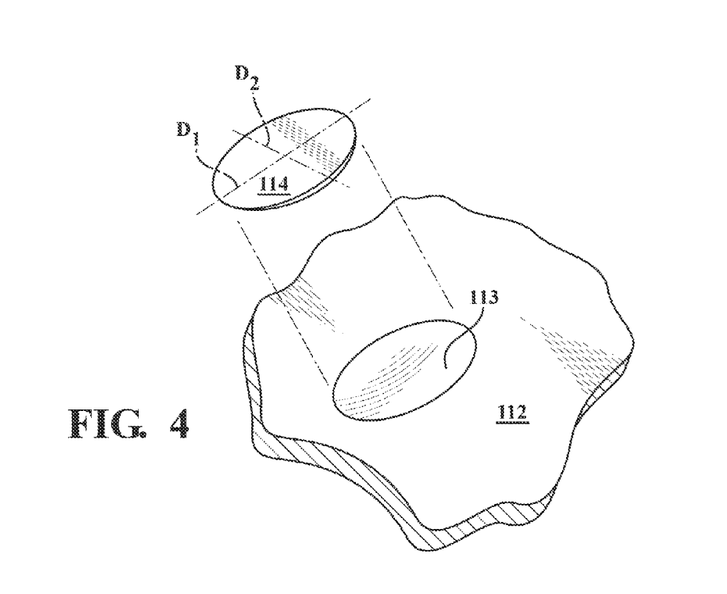
FIG. 4 is a perspective view of a substrate after removal of a sample and the sample removed from the substrate.

As described above, the shape of the cutter 70 is defined by the radius of curvature $R_C$. As seen in a cross-section through the center of the cutter 70 extending in the longitudinal direction, the shape of the cutter 70 comprises a hemi-ellipsoidal or semi-ellipsoidal shape. The semi-ellipsoidal cutter 70 is adapted to remove an elliptically shaped surface portion of a base material or substrate 112, to form a collection sample 114, as seen in FIG. 4. Specifically, the semi-ellipsoidal configuration of the cutter 70 permits the cutter 70 to cut an elongated sample 114 from a substrate 112 in such a way that a shallow cut 113 into the substrate 112 may be performed, while providing a substantial amount of material in the sample 114, in that the sample 114 is formed having an elongated dimension, i.e., with a major dimension $D_1$ substantially greater than a minor dimension $D_2$, and may have a generally elliptical shape.

Figure 5:
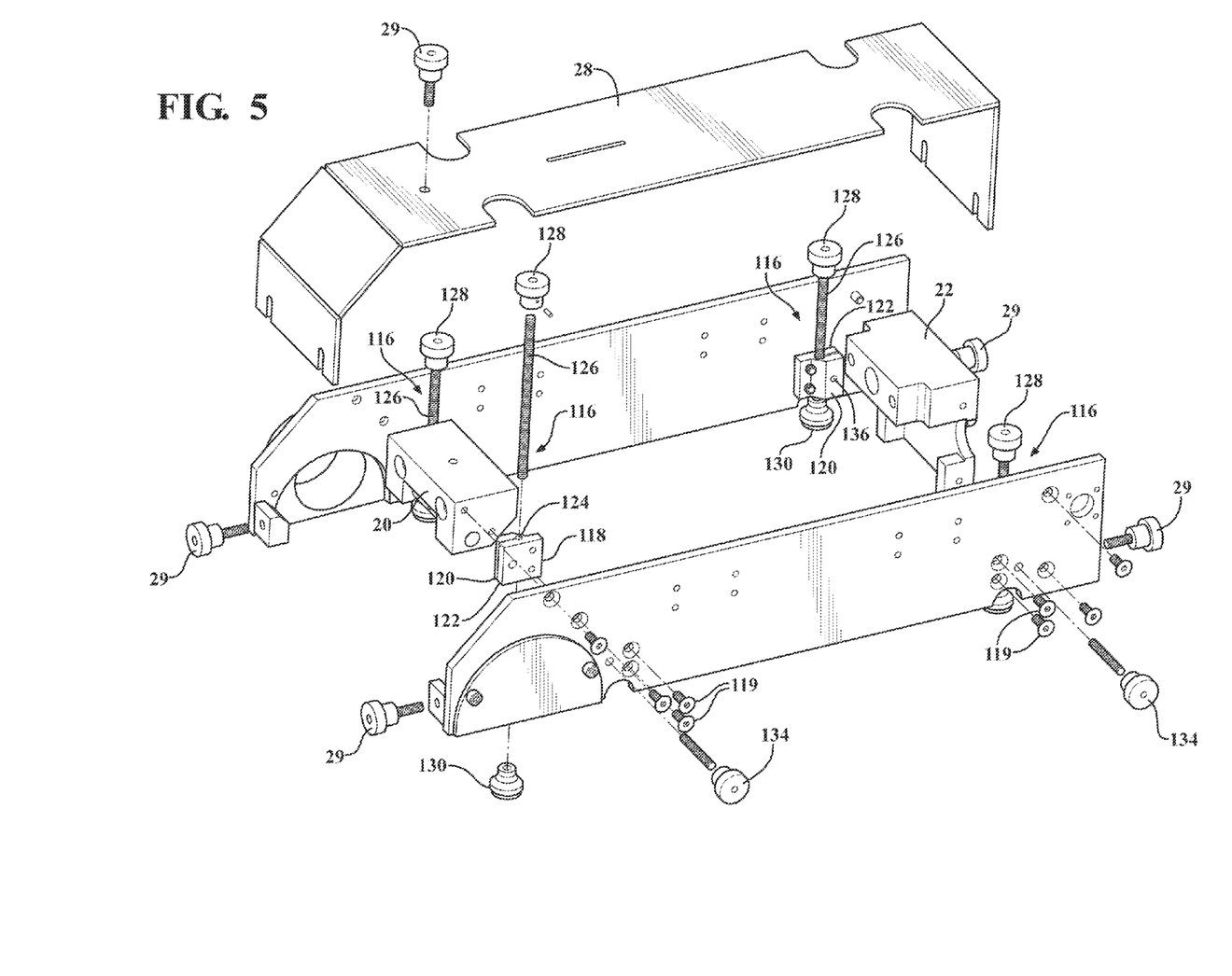
FIG. 5 is an exploded view of a frame structure and illustrating a height adjustment structure for the sampling device.

Referring to FIG. 5, a height adjustment structure is provided comprising a plurality of height adjusting members 116, illustrated herein as four height adjusting members 116. Each height adjusting member 116 includes an adjustment clamp 118 that is mounted to an inside surface of one of the first and second side portions 24, 26, such as by fasteners 119. Each adjustment clamp 118 includes a pair of clevis plates 120, 122 and a threaded aperture 124 at a juncture between the clevis plates 120, 122. A threaded rod 126 is engaged through the threaded aperture 124. A knob 128 is affixed to an upper end of the rod 126, and a leveling foot 130 is mounted to a lower end of the rod 126. The leveling foot 130 may comprise a ball and socket joint, or similar joint to permit the foot 130 to pivot relative to the rod 126, such as to accommodate irregular or sloped surfaces.

The rod 126 may be manually rotated at the knob 128 to move the rod 126 and respective foot 130 vertically relative to the frame structure 16. Thus, the adjusting members 116 may be operated to adjust the height of the frame structure 116, and therefore the cutter 70, relative to the substrate 112 to control the depth of a sampling cut 113 performed by the cutter 70. A lock screw 134 may extend through a threaded aperture 136 of the clevis plate 120 in each adjustment clamp 118 to draw the clevis plate 120 toward the clevis plate 122 in order to lock the rod 126 at a selected position relative to the adjustment clamp 118.

Figure 6:
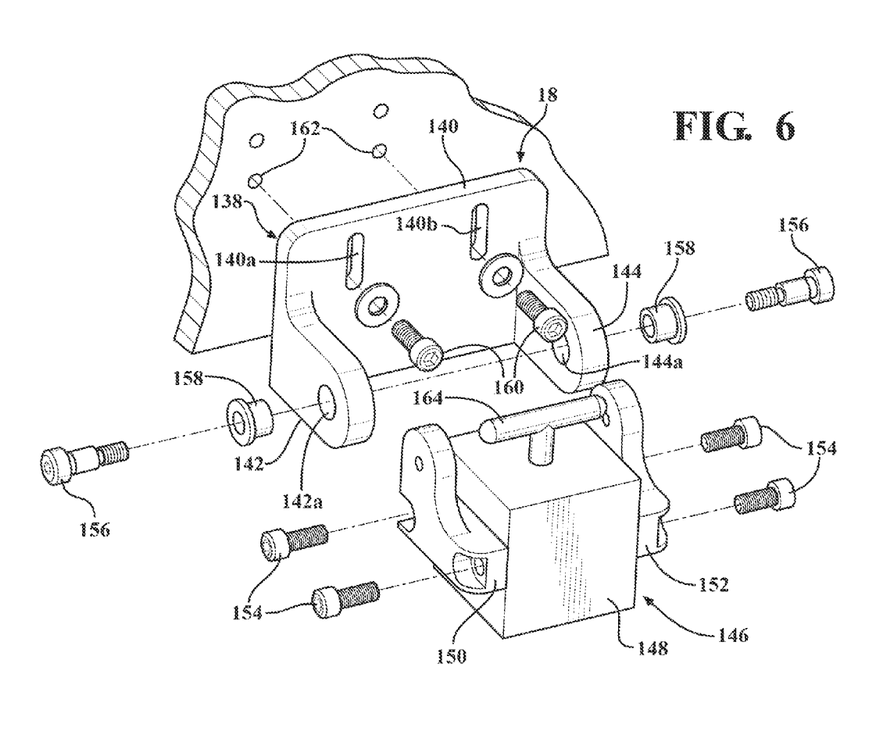
FIG. 6 is an exploded view of a clamp member for the sampling device.

Referring to FIG. 6, one of the clamp members 18 is illustrated and includes a U-shaped mount bracket 138 comprising a base plate 140 and a pair of mount arms 142, 144. A magnet assembly 146 is supported between the mount arms 142, 144 and includes a magnet 148 and first and second magnet brackets 150, 152 mounted to either side of the magnet 148 by screws 154. The magnet brackets 150, 152 are pivotally supported to the mount arms 142, 144 by shoulder bolts 156 that extend through bushings 158 in apertures 142a, 144a of the mount arms 142, 144. The pivotal mounting of the magnet brackets 150, 152 permit pivotal movement of the magnet assembly 146 relative to the frame structure 16 to accommodate various orientations of the substrate surface in the local area of the magnet 148.

The mount plate 140 includes a pair of slots 140a, 140b, each of which receives a screw 160. The screws 160 are engaged in threaded apertures 162 in one of the side portions 24, 26 for affixing the mount bracket 138 to a respective side portion 24, 26. The screws 160 operate as releasable locking members that may be loosened to permit the clamp member 18 to be adjusted vertically relative to the frame structure 16, as is described further below.

The magnet 148 preferably comprises a switchable magnet and includes a handle 164 that may be rotated to increase or decrease the external magnetic field of the magnet 148, permitting attachment to and detachment from a substrate surface. The magnet 148 may comprise a switchable magnet sold under the name MagSquare by Magswitch Technology Inc. of Littleton, Colo.

In a sampling operation using the sampling device 10, the sampling device 10 may be positioned on a surface 166 (FIG. 3) of a substrate 112 from which a sample is to be taken. In one contemplated use of the sampling device 10, a sample may be taken from a substrate comprising a magnetic material, such as Inconel®. The configuration or shape of the surface 166 that the sampling device 10 is used on is not limited to any particular contour and may be, for example, an interior surface of a pipe, an exterior surface of a pipe or a flat surface.

The thickness of the sample obtained from the substrate by the sampling device 10 may be controlled by adjusting the height adjusting members 116. In particular, the knobs 128 on the threaded rods 126 of the height adjusting members 116 may be rotated to position each of the leveling feet 130 for engagement with the surface 166, and to position the frame structure 16 at a predetermined distance from the surface 166 at the location of each of the leveling feet 130. The individual adjustment of the height adjusting members 116 facilitates precise vertical positioning of the sampling device 10, such as to compensate for irregular surfaces or curvature of a surface.

After the height of the frame structure 16 relative to the surface 166 is established, the clamp members 18 may be positioned vertically relative to the side portions 24, 26 of the frame structure 16. That is, the screws 160 may be loosened such that the base plate 140 of each clamp member 18 may move along the extent defined by the slots 140a, 140b to position a bottom surface of each of the magnets 148 in engagement with a portion of the surface 166. The magnet brackets 150, 152 may pivot at the shoulder bolts 156 during vertical adjustment of the clamp members 18, such that the magnets 148 may be positioned to rest substantially flat on an adjacent portion of the surface 166. With the magnets 148 thus in position on the surface 166, the screws 160 may be tightened and the magnet handles 164 may be rotated to affix the sampling device 10 substantially immovably in position on the substrate 112 via the external magnetic field applied through the magnets 148. The magnets 148 preferably may provide a combined holding force of approximately 600 lbs. to provide secure stationary positioning of the sampling device 10.

Figure 7:
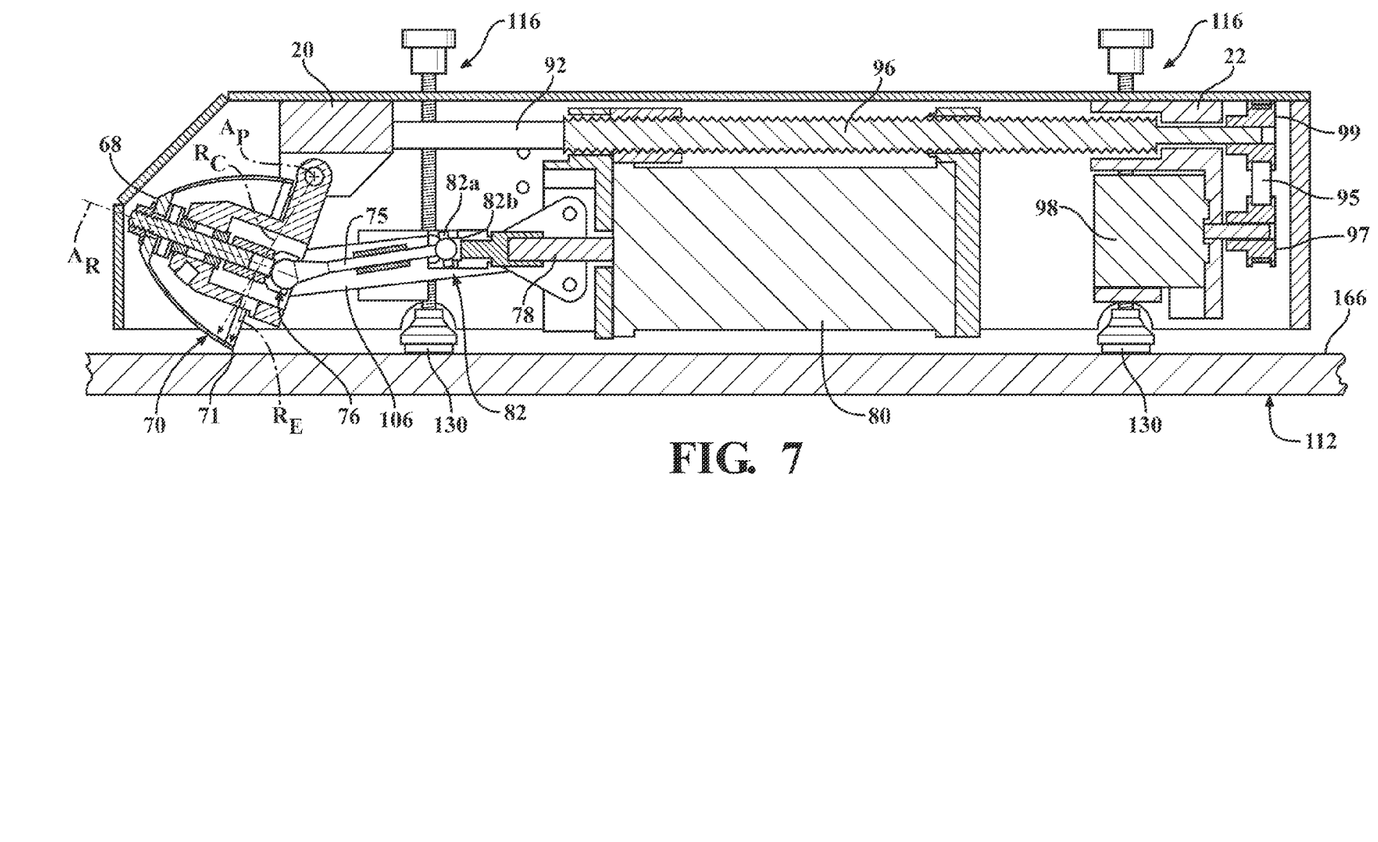
FIG. 7 is a view similar to FIG. 3 and showing the cutter head assembly with the cutter located in a position prior to a cutting operation.

A cutting operation is performed by the cutter 70 by first locating the cutter 70 in a forwardly pivoted position, as shown in FIG. 7, and is preferably located in this position prior affixing the sampling device to the substrate 112. The motor 80 is actuated to drive the cutter 70 in rotational movement, and the stepper motor 98 is actuated to rotate the screw shaft 96 to draw the motor assembly 81 rearwardly. As the motor assembly 81 moves rearwardly, the cutting end 71 is caused to engage and move through the substrate 112 in an arc defined by the pivot body 32 and the diameter of the cutter 70 and extending below the base side 30. In particular, the pivot links 104 provide a force to pivot the pivot body 32 rearwardly with rearward movement of the motor assembly 81. The cutter end 71 removes sufficient material to provide a clearance for the remainder of the cutter 70 as the cutter 70 follows an arc to the opposite or exit end of the cut. FIG. 3 illustrates a position of the cutter 70 approximately half way through the cutting operation.

It may be noted that the cutter shaft housing 44 may be provided with a magnet 168 (FIG. 2), located in a lower portion of the cutter shaft housing 44. The magnet 168 is positioned to be located adjacent to the sample 114 as it is cut from the substrate 112, and may attract and hold the sample 114 as the cutting operation concludes and the sample 114 is released from the substrate 112.

The cutting end 71 traces an elliptical path through the substrate 112 to cut out a sample 114 generally shaped as an ellipse, as illustrated in FIG. 4. The elliptically shaped sample 114 that may be removed from the substrate 112 by the present sampling device 10 provides a substantial amount of sampled material for use in testing the material of the substrate 112, while providing a shallower cut 113 into the substrate 112. That is, a relatively long arc for the path of the cutter 70, permits a longer length dimension for the sample 114 relative its thickness, with a corresponding reduced impact due to removal of material. Hence, any detrimental structural effects produced by the sampling device 10, such as structural weakening with removal of material, may be reduced relative to prior devices for removing samples.

Further, the stepper motor 98 is operated at a relatively slow speed, such that the cutter 70 is swept through the substrate at a slow speed, allowing heat to be dissipated through the cutter 70 and substrate 112, avoiding elevated temperatures of the sample 114 that could otherwise alter the grain structure of the material, and preferably maintains the temperature of the sample 114 below about 200° F. In a particular example, the cutter 70 may be used to cut a sample 114 having a length dimension of approximately 45 mm over a time period of 90 minutes, such that the cutter is advanced approximately 0.5 mm per minute. Providing a slow advance speed for the cutter 70 and avoiding elevated temperatures helps to ensure that the sample 114 is removed without substantially altering its physical characteristics, to provide an accurate representation of the material of the substrate 112 for testing. In addition, the slow advance speed of the cutter, and associated lower temperature for the sample 114, enables the present sampling device 10 to be operated without a coolant, such as a cooling fluid, minimizing the size of the sampling device 10 to facilitate operation in smaller spaces.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A sampling device for removing a surface portion from a substrate, the device comprising:
    a frame structure;
    a cutter head assembly comprising:
        a pivot body having a first end supported at a pivot point on said frame structure;
        a cutter supported for rotation about a rotational axis at a second end of said pivot body, said cutter comprising a shape defined by a rotation of a conic having a circular cutting end, wherein said shape of said cutter comprises a semi-ellipsoidal shape adapted to remove an elliptically shaped surface portion from said substrate;
    a drive motor operably connected to said cutter; and
    said pivot point located in spaced relation to said rotational axis, and said cutter being operable to cut a surface portion of a substrate during pivotal movement about said pivot point.

2. The sampling device of claim 1, wherein said pivot point is located a distance from said rotational axis that is greater than a radius of said circular cutting end.

3. The sampling device of claim 1, wherein said drive motor is movable relative to said frame structure in a longitudinal direction, and including a linkage between said drive motor and said pivot body, said linkage transmitting longitudinal movement of said drive motor into pivotal movement of said pivot body.

4. The sampling device of claim 3, including a drive shaft extending adjacent to said linkage for transmitting rotational movement from said drive motor to said cutter.

5. The sampling device of claim 3, including a stepper motor operably coupled to said drive motor to move said drive motor in said longitudinal direction.

6. The sampling device of claim 1, including adjusting members movable relative to said frame structure to define an adjustable predetermined depth for said cutter to penetrate said substrate.

7. The sampling device of claim 1, including clamp members comprising magnets mounted to said frame structure for engagement with said substrate.

8. The sampling device of claim 7, wherein said frame structure includes a housing assembly having side portions, said clamp members being slidably positionable along said side portions, and including locking members adapted to lock said clamp members to predetermined positions along said side portions.

9. A sampling device for removing a surface portion from a substrate, the device comprising:
    a frame structure including a base side and a housing assembly having side portions;
    a cutter mechanism including a cutter movable in a vertical direction to extend from said base side into engagement with said substrate;
    a plurality of height adjusting members extending from said base side to engage said substrate, said height adjusting members being movable relative to said frame structure and relative to said cutter to define an adjustable predetermined depth for said cutter to penetrate said substrate; and
    a plurality of clamp members comprising magnets mounted to said side portions of said frame structure for engagement with said substrate to retain said frame structure at predetermined height positions relative to said substrate, as defined by said height adjusting members, wherein said clamp members are adjustable in said vertical direction along said side portions to positions corresponding to said predetermined height positions.

10. The sampling device of claim 9, including a locking member associated with each of said clamp members, said locking members adapted to lock said clamp members to said side portions at said predetermined height positions.

11. The sampling device of claim 9, wherein said clamp members are supported for pivotal movement relative to said frame structure.

12. The sampling device of claim 9, wherein said magnets comprise switchable magnets.

13. The sampling device of claim 9, wherein said cutter mechanism is included in a cutter head assembly comprising:
   a pivot body having a first end supported at a pivot point on said frame structure;
   a cutter supported for rotation about a rotational axis at a second end of said pivot body, said cutter comprising a shape defined by a rotation of a conic having a circular cutting end; and
   including a drive motor operably connected to said cutter for driving said cutter in rotational movement.

14. The sampling device of claim 13, wherein said shape of said cutter comprises a semi-ellipsoidal shape adapted to remove an elliptically shaped surface portion from said substrate.

15. The sampling device of claim 14, wherein said pivot point is located in spaced relation to said rotational axis and defines a center of curvature for a surface of said cutter.

16. The sampling device of claim 15, wherein said pivot point is located a distance from said rotational axis that is greater than a radius of said circular cutting end.

17. The sampling device of claim 13, wherein said drive motor is movable relative to said frame structure in a longitudinal direction, and including a linkage between said drive motor and said pivot body, said linkage transmitting longitudinal movement of said drive motor into pivotal movement of said pivot body.

* * * * *